US005633362A

United States Patent [19]
Nagarajan et al.

[11] Patent Number: 5,633,362
[45] Date of Patent: May 27, 1997

[54] PRODUCTION OF 1,3-PROPANEDIOL FROM GLYCEROL BY RECOMBINANT BACTERIA EXPRESSING RECOMBINANT DIOL DEHYDRATASE

[75] Inventors: Vasantha Nagarajan, Wilmington; Charles E. Nakamura, Claymont, both of Del.

[73] Assignee: E. I. Du Pont de Nemours and Company, Wilmington, Del.

[21] Appl. No.: 440,377

[22] Filed: May 12, 1995

[51] Int. Cl.$^6$ .................. C07H 21/02; C07H 21/04; C12N 1/21
[52] U.S. Cl. .................. 536/23.1; 536/22.1; 536/24.3; 435/252.3; 435/252.33
[58] Field of Search ................ 536/22.1, 23.1, 536/24.3; 435/252.3, 252.33

[56] References Cited

U.S. PATENT DOCUMENTS

| | | | |
|---|---|---|---|
| 4,935,554 | 6/1990 | Murphy et al. | 568/867 |
| 4,962,027 | 10/1990 | Slininger et al. | 435/147 |
| 5,015,789 | 5/1991 | Arntz et al. | 568/862 |
| 5,164,309 | 11/1992 | Gottschalk et al. | 435/158 |
| 5,246,843 | 9/1993 | Kasai et al. | 435/158 |
| 5,254,467 | 10/1993 | Kretschmann et al. | 435/158 |

FOREIGN PATENT DOCUMENTS

WO93/25696  12/1993  WIPO .............. C12P 7/18

OTHER PUBLICATIONS

Gibco–BRL catalog (1993–1994) pp. 9–5.
Daniel et al, (Apr. 1995), "Purification of 1,3–propanediol dehydrogenase from *Citrobacter freundii* and cloning, sequencing and overexpression of the corresponding gene in *Escherichia coli*", J. Bacteriol. 177(8):2151–2156.

Daniel et al, *FEMS Microbiol. Lett.*, 100, 281–286 (1992).

Forage, R.G. et al, *Bacteriology*, 149(2), 413–419 (1982).

Jeter, R.M., *J. Gen. Microbiology*, 136, 887–896 (1990).

Tong, I–T et al, *Appl. and Environmental Microbiology*, 57(12), 3541–3546 (1991).

Ichikawa et al, *J. Ferment. Technol.*, 63(2), 135–141 (1985).

Sprenger, G.A. et al, *J. Gen. Microbiology*, 135, 1255–1262 (1989).

Boenigk, R. et al, *Appl. Microbiol. and Biotechnol.*, 38, 453–457 (1993).

Forsberg, C.W., *Appl. Environ. Microbiol.*, 53(4), 639–643 (1987).

Zeng, A–P. et al, *Enzyme Microb. Technol.*, 15, 770–779 (1993).

Bobik, T.A. et al, *J. of Bacteriol.*, 174(7), 2253–2266 (1992).

Hartmanis, M.G.N. et al, *Archives of Biochem. and Biophysics*, 245(1), 144–152 (1986).

Tobimatsu, T. et al, *J. Biol. Chem.*, 270(13), 7142–7148 (1995).

*Primary Examiner*—Stephanie W. Zitomer
*Assistant Examiner*—Jeffrey Fredman

[57] ABSTRACT

A process is provided for the bioconversion of glycerol to 1,3-propanediol in which genes from a bacteria known to possess a diol dehydratase enzyme for 1,2-propanediol degradation are cloned into a bacterial host and the host is grown in the presence of glycerol; expression of the foreign genes in the host cell facilitates the enzymatic conversion of glycerol to 1,3-propanediol which is isolated from the culture.

10 Claims, 4 Drawing Sheets

```
Klebsiella    ---->1 MRSKRFEALAKRPVNQDGFVKEWIEEGFIAMESPNDPKPSIRIVNGAVTE 50
                     |||||||||||||||||||||||||||||||||||||||||||:|||||||
Salmonella    ---->1 MRSKRFEALAKRPVNQDGFVKEWIEEGFIAMESPNDPKPSIKIVNGAVTE 50

51 LDGKPVEQFDLIDHFIARYGINLARAEEVMAMDSVKLANMLCDPNVKRSD 100
                 ||||||.:|
              51 LDGKPVSEF......................................... 59
```

```
pduC_Kp  ----> 1  M.RSKRFEALAKRPVNQDGFVKEWIEEGFIAMESPNDPKPSIRIVNGAVT  49
                  | |||||| .||.||||||||::  ||  |||:|||||  ||  .|:::  || :.
dhaB_Cf  ---->  1 MRRSKRFEVLAQRPVNQDGLIGEWPEEGLIAMESPYDPASSVKVENGRIV  50

50 ELDGKPVEQFDLIDHFIARYGINLARAEEVMAMDSVKLANMLCDPNVKRS  99
               |||||.  .:||:||:|||  |:||::  ||  .|.:|.:.::|.||.| :|.|.
            51 ELDGKSRAEFDMIDRFIADYAINVPEAERAMQLDALEIARMLVDIHVSRE 100

100 DIVPLTTAMTPAKIVEVVSHMNVVEMMMAMQKMRARRTPSQQAHVTNIKD 149
               :|:::|||:||||  :||:.:|||||||||||:||||||||||.|.||||:||
           101 EIIAITTAITPAKRLEVMAQMNVVEMMMALQKMRARRTPSNQCHVTNLKD 150

150 NPVQIAADAAEGAWRGFDEQETTVAVARYAPFNAIALLVGSQVGRPGVLT 199
               ||||||||||::  |||.|||||||::|||||||||:||||||.| |||||
           151 NPVQIAADAAEAGIRGFSEQETTVGIARYAPFNALALLVGSQCGAPGVLT 200

200 QCSLEEATELKLGMLGHTCYAETISVYGTEPVFTDGDDTPWSKGFLASSY 249
               |||:|||||.|||  |  |:||||||.||||||||||||||||:|||| .|
           201 QCSVEEATELELGMRGLTSYAETVSVYGTESVFTDGDDTPWSKAFLASAY 250

250 ASRGLKMRFTSGSGSEVQMGYAEGKSMLYLEARCIYITKAAGVQGLQNGS 299
               ||||||||:|||.|||. |||.|:||||||.|||:|||:|||:|||||||||.
           251 ASRGLKMRYTSGTGSEALMGYSESKSMLYLESRCIFITKGAGVQGLQNGA 300

300 VSCIGVPSAVPSGIRAVLAENLICSALDLECASSNDQTFTHSDMRRTARL 349
               |||||:..:||||||||||||||||.|  ||||.||.|||||.|||:|||||
           301 VSCIGMTGAVPSGIRAVLAENLIASMLDLEVASANDQTFSHSDIRRTART 350

350 LMQFLPGTDFISSGYSAVPNYDNMFAGSNEDAEDFDDYNVIQRDLKVDGG 399
               |||:||||||  ||||||||||||||||||  |||||||||::|||| .||||
           351 LMQMLPGTDFIFSGYSAVPNYDNMFAGSNFDAEDFDDYNILQRDLMVDGG 400

400 LRPVREEDVIAIRNKAARALQAVFAGMGLPPITDEEVEAATYAHGSKDMP 449
               ||||  ||:.||||||||||:||||  ::|||  |.||||:||||||||||.|||||
           401 LRPVTEEETIAIRNKAARAIQAVFRELGLPLISDEEVDAATYAHGSKDMP 450

450 ERNIVEDIKFAQEIINKNRNGLEVVKALAKGGFPDVAQDMLNIQKAKLTG 499
               .||:|||   .:|::..:|  .||:|  ||..:||.|:|   ::||:   :.::||
           451 ARNVVEDLAAVEEMMKRNITGLDIVGALSSSGFEDIASNILNMLRQRVTG 500

500 DYLHTSAIIVGEGQVLSAVNDVNDYAGPATGYRLQGERWEEIKNIPGALD 549
               |||:||||:    : :|:|||||:|||.||||||: :|||.||||||:|.::
           501 DYLQTSAILDRQFDVVSAVNDINDYQGPGTGYRISAERWAEIKNIAGVVQ 550
           550 PNELG* 555
                |..::
           551 PGSIE* 556
```

```
dhaB_Kp. ---►    1 .............RAVLAENLIASMLDLEVASANDQTFSHSDIRRTART  36
                      |||||||||||||||||||||||||||||||||||||
dhaB_Cf. ---►  301 VSCIGMTGAVPSGIRAVLAENLIASMLDLEVASANDQTFSHSDIRRTART 350

37 LMQMLPGTDFIFSGYSAVPNYDNMFAGSNFDAEDFDDYNILQRDLMVDGG  86
                 ||||||||||||||||||||||||||||||||||||||||||||||||||
             351 LMQMLPGTDFIFSGYSAVPNYDNMFAGSNFDAEDFDDYNILQRDLMVDGG 400

87 LRPVTEAETIAIRQKAARAIQAVFRELGLPPIADEEVEAATYAQG.....  131
                 ||||||.||||||.|||||||||||||||| |.||||:|||||:|
             401 LRPVTEEETIAIRNKAARAIQAVFRELGLPLISDEEVDAATYAHGSKDMP 450
```

PRODUCTION OF 1,3-PROPANEDIOL FROM GLYCEROL BY RECOMBINANT BACTERIA EXPRESSING RECOMBINANT DIOL DEHYDRATASE

FIELD OF INVENTION

This invention relates to a process for the bioconversion of glycerol to 1,3-propanediol by recombinant bacteria harboring a foreign gene encoding a diol dehydratase.

BACKGROUND 1,3-Propanediol is a monomer having potential utility in the production of polyester fibers and the manufacture of polyurethanes and cyclic compounds.

A variety of chemical routes to 1,3-propanediol are known. For example, 1,3-propanediol may be prepared from ethylene oxide and a catalyst in the presence of phosphine, water, carbon monoxide, hydrogen and an acid; by the catalytic solution phase hydration of acrolein followed by reduction; or from hydrocarbons such as glycerol, reacted in the presence of carbon monoxide and hydrogen over periodic table group VIII catalysts. Although it is possible to generate 1,3-propanediol by these methods, they are expensive and generate waste streams containing environmental pollutants.

Biological routes to 1,3-propanediol are known which utilize feedstocks produced from renewable resources. For example, bacterial strains able to convert glycerol into 1,3-propanediol are found e.g., in the species Klebsiella, Citrobacter, Clostridium, and Lactobacillus. In these bacteria, glycerol can enter either an oxidative or reductive pathway. Oxidation of glycerol results in the conversion of glycerol to dihydroxyacetone (DHA) by glycerol dehydrogenase and the DHA is phosphorylated by an adenosine triphosphate (ATP) dependent kinase to yield dihydroxyacetone phosphate (DHAP) which enters the glycolytic pathway in the cell. Reduction of glycerol is accomplished by an initial isomerization and dehydration catalyzed by glycerol dehydrates to yield 3-hydroxypropionaldehyde which is further reduced by 1,3-propanediol:NAD$^+$ oxidoreductase to yield 1,3-propanediol, a dead end cellular metabolite. The expression of at least the first two enzymes involved in the oxidative pathway as well as the two enzymes involved in the reductive pathway in *K. pneumoniae* are coordinately regulated. The four enzyme system is functionally linked where the production of 1,3-propanediol from glycerol is dependent on the presence of the reductants supplied by the DHA to DHAP pathway.

The genes responsible for the conversion of glycerol to 1,3-propanediol have been isolated and are all encompassed by the dha regulon. In order to make use of the potential advantages of higher protein expression and growth rate of recombinant bacteria, several attempts have been made to express the dha regulon as heterologous genes in *E. coli*. For example, the dha regulon from Citrobacter (Daniel et al., *FEMS Microbiol. Lett.*, 100, 281, (1992)) and Klebsiella (Tong et al., *Appl. Environ. Microbiol.*, 57, 3541, (1991); have been expressed in *E. coli* and have been shown to convert glycerol to 1,3-propanediol. The expression of the dha regulon in recombinant bacteria offers potential advantages over wild type production of 1,3-propanediol. The genes involved in the dha regulon provide both the enzymes and the necessary reductants needed for the efficient conversion of glycerol to 1,3-propanediol. However, simultaneous overexpression of both glycerol dehydrogenase and glycerol dehydrates results in some of the glycerol being converted to DHA. It would be advantageous to convert all the glycerol to 1,3-propanediol by expressing only the reductive pathway enzymes while providing a different substrate for the generation of reductant. A preferred system would provide for a more efficient use of the glycerol substrate while maintaining high yields of diol product.

It has long been known that a number of bacteria are capable of using 1,2-propanediol is a sole carbon source. It is thought that this ability is conferred by a specific vitamin $B_{12}$ dependent diol dehydratase which is encoded by the pdu operon. The pdu operon is linked to the cob operon which encodes enzymes needed for the biosynthesis of vitamin $B_{12}$ and both operons are subject to the regulation of the same activator protein encoded by the c pocR gene.

Recently the genes encoding the diol dehydratase of *Klebsiella oxytoca* were cloned and sequenced and the genes were expressed in *E. coli*. Although active diol dehydratase was observed in these transformants, there is no evidence that these clones are able to metabolize a carbon substrate to 1,3-propanediol.

Various Salmonella and Klebsiella sp. are known to produce a diol dehydratase which catalyzes the conversion of 1,2-propanediol, under anaerobic conditions, to propionaldehyde and eventually to 1-propanol and propionic acid. The diol dehydratase has also been identified in Clostridia, and Propionibacterium but not in *E. coli*. The diol dehydratase from Klebsiella sp. can convert glycerol to 1,3-propanediol (Forage et al., Bacteriol, 149, 413 (1981)).

Although the primary function of the pdu diol dehydratase is in the metabolism of 1,2-propanediol, applicants have discovered that the expression of *K. pneumoniae* diol dehydratase in *E. coli* will catalyze the conversion of glycerol to 1,3-propanediol. The recombinant bacteria expressing the dial dehydratase pathway converts glycerol to the desired 1,3-propanediol product and is not dependent on a linked system as with the glycerol dehydratase system. Applicants have discovered that transformation of recombinant bacteria with the pdu diol dehydratase genes from Klebsiella sp. affords a new, efficient and cost effective biological route to 1,3-propanediol.

SUMMARY OF THE INVENTION

The present invention comprises a cosmid comprising a DNA fragment of about 35 kb isolated from *Klebsiella pneumoniae* wherein said fragment encodes an active diol dehydrates enzyme having the restriction digest in FIG. 5, columns numbered 4.

The present invention further comprises a transformed microorganism comprising a host micro-organism and the above-described cosmid.

The present invention further comprises a gene encoding an active diol dehydratase enzyme having the DNA sequence as listed in SEQ ID NO.: 1 or a gene encoding an active alcohol dehydrogenase having the DNA sequence as listed in SEQ ID NO.: 2.

The present invention further comprises a transformed microorganism comprising a host micro-organism and either of the above-described genes.

The present invention further comprises the bioconversion of a carbon substrate by transforming a microbial host with genes capable of expressing a diol dehydratase and contacting said transformed host with said substrate.

The present invention further comprises the bioconversion of a carbon substrate by transforming a microbial host with genes derived from a cosmid comprising a fragment of about 35 kb isolated from *Klebsiella pneumoniae* wherein said genes encode an active diol dehydratase enzyme and any other functional bacterial protein encoded by said cosmid, and contacting said transformed host with said substrate.

BRIEF DESCRIPTION OF THE FIGURES

FIG. 3 is a comparison of amino acid sequence coded by pduC gene of *K. pneumoniae* (SEQ ID NO.: 5) with that of glycerol dehydratase from *Citrobacter freundii* (SEQ ID NO.: 6) showing percent similarity and percent identity.

FIG. 4 is a comparison of the amino acid sequence deduced from an open reading frame of the glycerol dehydratase gene from *K. pneumoniae* (SEQ ID NO.: 7) with the amino acid sequence encoded by the same gene from *Citrobacter freundii* (SEQ ID NO.: 8). The figure shows the percent similarity and percent identity between the two deduced amino acid sequences.

DETAILED DESCRIPTION OF THE INVENTION

Figures 1, 2:
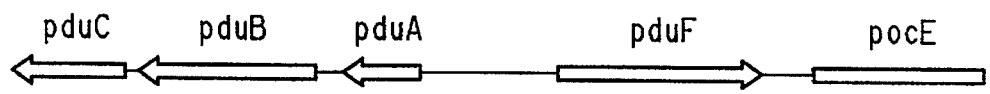
FIG. 1 is a schematic representation of the gene organization of pdu-cob region of *K. pneumoniae*. The DNA sequence was analyzed using the GCG-Wisconsin package and the open reading frames were compared to the *S. typhimurium* sequence using GAP. The percent identity and similarity are shown.
FIG. 2 is a comparison of the amino acid sequence encoded by the pduC gene of *S. typhimurium* (SEQ ID NO.: 3) with the amino acid sequence encoded by the pduC gene of *K. pneumoniae* (SEQ ID NO.: 4).

As used herein the following terms may be used for interpretation of the claims and specification.

The term "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" or "transfection" refers to the acquisition of new genes in a cell after the incorporation of nucleic acid.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "plasmid" or "vector" or "cosmid" as used herein refers to an extra chromosomal element often carrying genes which are not part of the central metabolism of the cell, and usually in the form of circular double-stranded DNA molecules.

The term "carbon substrate" means any carbon source capable of being metabolized by a microorganism wherein the substrate contains at least one carbon atom.

The term "dehydratase enzyme" will refer to any enzyme that is capable of converting a glycerol molecule to the product 3-hydroxypropionaldehyde. For the purposes of the present invention the dehydratase enzymes are either a glycerol dehydratase or a diol dehydratase having preferred substrates of glycerol and 1,2-propanediol, respectively.

The term "1,3-propanediol" refers to a compound of the formula $HOCH_2—CH_2—CH_2OH$, useful as a monomer in the production of polymers for fiber manufacture.

The following strains were deposited under the terms of the Budapest Treaty with the American Type Culture Collection (ATCC) (12301 Packlawn Drive, Rockville, Md. 20852, U.S.A.): ATCC 69789 corresponds to *E. coli* DH5α containing cosmid pKP1. ATCC 69790 refers to *E. coli* DH5α containing cosmid pKP4.

The present invention comprises a process for a biological production of 1,3-propanediol from glycerol using recombinant organisms. The process incorporates a transformed *E. coli* bacteria, transformed with a heterologous pdu diol dehydratase gene, having a specificity for 1,2-propanediol. The transformed *E. coli* is grown in the presence of glycerol as a carbon source and 1,3-propanediol is isolated from the growth media.

The process of the present invention provides a rapid, inexpensive and environmentally responsible source of 1,3-propanediol monomer useful in the production of polyesters and other polymers.

The invention provides a transformed host cell suitable for the expression of pdu diol dehydratase. Suitable host cells will generally be those that do not normally harbor a diol dehydratase gene. Preferred in the process of the present invention are *E. coli*, *Bacillus subtilis*, *Bacillus licheniformis* or *Pichia pastoris*. The diol dehydratase within the transformed host cell has been previously described by Toraya et al., *J. Biol. Chem.*, 252, 963, (1977).

Isolation of Genes

The pdu diol dehydratase gene is obtained from any suitable source, but preferably from a bacteria known to be able to use 1,2-propanediol as a sole carbon source. Suitable bacteria known to harbor the pdu gene include but are not limited to Klebsiella sp., Clostridia sp., Salmonella sp., and Citrobacter sp.

Methods of obtaining desired genes from a bacterial genome are common and well known in the art of molecular biology. In the present invention virtually any method may be used to isolate the gene encoding the desired diol dehydratase. For example, if the sequence of the gene is known, suitable genomic libraries created by restriction endonuclease digestion may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively cosmid libraries may be created where large segments of genomic DNA (35–45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. A number of cosmid vectors are known in the art such as pJB8 (Ish-Horowicz et al., Nucl. Acids Res. 9, 2989 (1981)), containing an amp marker, ColE1 origin of replication and a singel cos site; and, c2RB (Bates et al., Gene, 26, 137, (1983)), containing 2 cos sites, both kanamycin and ampicillin resistance genes and the ColE1 origin of replication. Although any cosmid vector is suitable for use in the present invention the vector Supercos 1 provided by Stratagene (La Jolla, Calif.) is most preferred.

Typically, to clone cosmids, foreign DNA is isolated and ligated, using the appropriate restriction endonucleases, adjacent to the cos region of the cosmid vector. Cosmid vectors containing the linearized foreign DNA is then packaged in vitro in DNA packaging vehicle such as bacteriophage λ. During the packaging process the cos sites are cleaved and the foreign DNA is packaged into the head portion of the bacterial viral particle. These particles are then used to transfect suitable host cells such as E. coli. Once injected into the cell, the foreign DNA circularizes under the influence of the cos sticky ends. In this manner, large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from K. pneumoniae and K. aerogenes was isolated by methods well known in the art and digested with the restriction enzyme Sau3A for insertion into a cosmid vector Supercos 1 and packaged using GigapackII™ packaging extracts. Following construction of the vector E. coli XL1-Blue MR cells were transformed with the cosmid DNA. Transformants were screened for the ability to convert glycerol to 1,3-propanediol by growing the cells in the presence of glycerol and analyzing the media for 1,3-propanediol formation.

The DNA sequences generated from cosmid transformations named pKP4 and pKP5 were compared to DNA sequences in the Genbank data base. Several independent clones showing homology to pdu region of S. typhimurium were identified, suggesting that these transformants carried DNA encoding 1,2 propanediol utilizing enzymes including a 1,2-diol dehydratase gene. In contrast, in transformants named pKP1 and pKP2, an open reading frame showed extensive homology to the glycerol dehydratase gene from C. freundii, suggesting that these transformants containing DNA encoding the glycerol dehydratase gene.

Cells

The present invention further comprises a transformed host cell capable of converting a carbon substrate to 1,3-propanediol. As disclosed above, host cells may be transformed with a single gene, encoding the diol dehydratase, a series of specific genes encoding the diol dehydratase and other enzymes known to facilitate the process of bioconversion or with an entire cosmid DNA fragment. Preferred for use in the present invention is DH5α E. coli. However, it is contemplated that other cells will be amenable to transformation with the instant genes and will include, but are not limited to, other microorganisms such as Bacillus sp., Klebsiella sp., Citrobacter sp., Clostridia sp. and Pichia sp.

Carbon Substrate

The present invention provides a carbon substrate which is converted to the desired 1,3-propanediol end product via the enzymatic machinery of the transformed host organism. Virtually any carbon substrate that will serve as a substrate for a dehydratase enzyme is suitable for the present invention where alcohols are of greatest use. Preferred carbon substrates will include, but are not limited to, glycerol, ethyleneglycol, 1,2-propanediol, 1,2-butanediol, and 2,3-butanediol, wherein glycerol is most preferred.

Purification and Isolation of 1,3-Propanediol

Methods for the purification of 1,3-propanediol from fermentation media are known in the art. For example propanediols can be obtained from cell media by subjecting the reaction mixture to extraction with an organic solvent, distillation and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exclusion column using a mobile phase of 0.01N sulfuric acid in an isocratic fashion.

The following Examples are meant to illustrate the invention but are not intended to limit it in any way.

EXAMPLES

GENERAL METHODS

Restriction enzyme digestions, phosphorylations, ligations and transformations were done as described in Sambrook, J. et al., Molecular Cloning: A Laboratory Manual, Second Edition, Cold Spring Harbor Laboratory Press (1989). GeneClean (Stratagene, La Jolla, Calif.) was used to remove enzymes from restriction digests, as specified by the manufacturers. Restriction enzymes were obtained from New England Biolabs (Boston, Mass.) or Promega (Madison, Wis.) Growth media was obtained from GIBCO/BRL (Gaithersburg, Md.)

The meaning of abbreviations is as follows: "h" means hour(s), "min" means minute(s), "sec" means second(s), and "d" means day(s).

Media

Synthetic S12 medium was used in the screening of bacterial transformants for the ability to make 1,3-propanediol. S12 medium contains: ammonium sulfate, 10 mM; potassium phosphate buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM.

Synthetic S15 medium was also used in the screening of bacterial transformants for the ability to make 1,3-propanediol. S15 medium contains: ammonium sulfate, 10 mM; potassium phosphate buffer, pH 7.0, 1 mM; MOPS/KOH buffer, pH 7.0, 50 mM; $MgCl_2$, 2 uM; $CaCl_2$, 0.7 uM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM.

Isolation and Identification 1,3-Propanediol

The conversion of glycerol to 1,3-propanediol was monitored by HPLC. Analyses were performed using a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01N $H_2SO_4$ as moble phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by gas chromatography/mass spectrometry (GC/MS) with a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Cells

Host cells used for cosmid transformations were *E. coli* DH5α fully described in Jesse et al., Focus, 10, 69 (1988) and obtained from GIBCO/BRL.

Construction of *K. pneumoniae* and *K. aerogenes* cosmid libraries

*K. pneumoniae* (ATCC 25955) and *K. aerogenes* ((*K. pneumoniae* or *Aerobacter aerogenes*) ECL 2106) obtained from Dr. E. C. C. Lin, Harvard Medical School, Cambridge, Mass., and described in Ruch, F. E. and Lin, E. C. C., Journal of Bacteriology, Vol. 124, p. 348 (October 1975), were grown in 100 ml LB medium for 8 h at 37° C. with aeration. Bacteria (25 ml per tube) were centrifuged at 3,000 rpm for 15 min in a DuPont Sorvall GLC 2.B centrifuge at room temperature. The bacteria were pelleted and supernatant was decanted. The bacterial cell pellet was frozen at −20° C. The chromosomal DNA was isolated as outlined below with special care taken to avoid shearing of DNA (i.e., vortexing was avoided). One tube of bacteria was resuspended in 2.5 ml of 50 mM Tris-10 mM EDTA and 500 ul of lysozyme (1 mg/ml) was added. The pellet was gently resuspended and the suspension was incubated at 37° C. for 15 min. Sodium dodecyl sulfate was added to bring the final concentration to 0.5%. This resulted in the solution becoming clear. Proteinase K (50 ug/ml) was added and the suspension was incubated at 55° C. for 2 h. The tube was removed and transferred to an ice bath and sodium chloride was added to yield a 0.4M final concentration. Two volumes of ethanol were added to the liquid. A glass tube was inserted to the interface and the DNA was gently spooled. DNA was dipped into a tube containing 70% ethanol. After drying in vacuo, the DNA was resuspended in 500 ul of water and the concentration of DNA was determined spectrophotometrically. A diluted aliquot of DNA was run on a 0.5% agarose gel to determine the intact nature of DNA.

The chromosomal DNA was partially digested with Sau3A as outlined by Sambrook et al., *supra*. DNA (2 ug) was digested with 2 units of Sau3A (Promega, Madison, Wis.) at room temperature in 200 ul of total volume. At 0, 5, 10 and 20 min, samples (50 ul) were removed and transferred to tubes containing 5 umol of EDTA. These tubes were incubated at 70° C. for 10 min. An aliquot (2 ul) was withdrawn and analyzed on a 0.5% agarose gel electrophoresis to determine the level of digestion and the rest of the sample (48 ul) was stored at −20° C. The gel was stained with ethidium bromide and visualized under UV to determine the partial digestion of the chromosomal DNA. A decrease in the size of the chromosomal DNA with increase in time was observed showing that the decrease in the size of the chromosomal DNA is due to the action of Sau3A. DNA was extracted from rest of the sample by standard protocol methods (Sambrook et al., *supra*).

A cosmid library of partially digested DNA from *K. pneumoniae* or *K. aerogenes* was prepared using Supercos cosmid vector kit and Gigapack II™ packaging extracts using reagents purchased from Stratagene (La Jolla, Calif.). The instructions provided by the manufacturer were followed. The packaged *K. pneumoniae* contained $4 \times 10^4$ to $1.0 \times 10^5$ phage titer and the packaged *K. aerogenes* contained $1.2 \times 10^5$ phage per mL as determined by transfecting *E. coli* XL1-Blue MR.

Cosmid DNA was isolated from 6 of the *E. coli* transformants and found to contain large insert of DNA (25 to 30 kb).

Example 1

Screening *E. coli* strains, transformed with a cosmid library DNA from *K. pneumoniae* and containing the glycerol dehydratase enzyme that produce 1,3-propanediol Example 1 demonstrated the screening of transformed *E. coli* cells with cosmid library DNA from *K. pneumoniae* for the presence of an enzyme that converted glycerol to 1,3-propanediol. Sequencing of two positive clones revealed that each contained a gene with a high degree of homology to the gene encoding glycerol dehydratase.

Six transformation plates containing approximately 1,000 colonies of *E. coli* XL1-Blue MR transfected with *K. pneumoniae* DNA were washed with 5 ml LB medium and centrifuged. The bacteria were pelleted and resuspended in 5 ml LB medium+glycerol. An aliquot (50 ul) was inoculated into a 15 ml tube containing S12 synthetic medium with 0.2% glycerol+400 ng per ml of vitamin $B_{12}$+0.001% yeast extract+50 ug/ml ampicillin (50 amp). The tube was filled with the medium to the top, wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production were plated onto a LB+50 amp, and serial dilutions were performed in order to isolate single colonies. Forty-eight single colonies were isolated and checked again for the production of 1,3-propanediol. Cosmid DNA was isolated from 6 independent clones and transformed into *E. coli* strain DH5α. The transformants were again checked for the production of 1,3-propanediol. Two transformants were characterized further and designated as DH5α-pKP1 and DH5α-pKP2.

DNA sequence analyses of DH5α-pKP1 and DH5α-pKP2 showed the presence of both glycerol dehydrogenase and glycerol dehydratase genes. Furthermore, the glycerol dehydratase gene of the transformed *E. coli* shared 96% similarity and 95% identity to the glycerol dehydratase gene from *Citrobacter freundii* (FIG. 4). Thus, pKP 1 and 2 appeared to contain the dha regulon genes from *K. pneumoniae*.

Example 2

Screening *E. coli* strains, transformed with a cosmid library DNA from *K. pneumoniae* and containing the 1,2-propanediol dehydratase enzyme that produce 1,3-propanediol Example 2 demonstrated the screening of *E. coli* cells, transformed with cosmid library DNA from *K. pneumoniae*, for the presence of an active enzyme that enabled the conversion of glycerol to 1,3-propanediol. Sequencing of the positive clones revealed that each contained a gene with a high degree of homology to the gene encoding 1,2-propanediol dehydratase, encoded by the pdu operon.

Single colonies of E. coli XL1-Blue MR transfected with packaged cosmid DNA from K. pneumoniae were inoculated into microtiter wells containing 200 ul of S15 medium+0.2% glycerol+400 ng/ml of vitamin $B_{12}$+0.001% yeast extract+50 ug/ml ampicillin (50 amp). In addition to the microtiter wells, a master plate containing LB+50 amp was also inoculated. After 96 h, 100 ul was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB+50 amp and one of which had not. Single colonies were isolated from the two positive clones grown on LB+50 amp and verified for the production of 1,3-propanediol and designated as pKP4 and pKP5. Cosmid DNA was isolated from E. coli strains containing pKP4 and pKP5 and E. coli strain DH5α was transformed. Six independent transformants were verified for the production of 1,3-propanediol. E. coli strain DH5α containing pKP4 or pKP5 was able to convert glycerol to 1,3-propanediol as described below.

Production of 1,3-Propanediol with E. coli Strains DH5α-pKP4 and DH5α-pKP5

A 2 mL screw capped cyrogenic vial, filled to capacity with media, was inoculated with E. coli strain DH5α containing pKP4 or pKP5 and incubated at 30° C. The media was composed of S12 medium supplemented with 0.01% yeast extract, 0.008% casamino acids, 50 ug/mL ampicillin, 10 ug/mL kanamycin, 0.4 ug/mL vitamin $B_{12}$, and either 0.2% glycerol or 0.1% glycerol plus 0.1% D-glucose. Inoculation was performed directly from an agar plate culture (LB supplemented with 50 ug/mL ampicillin). After 66 hr, growth was determined by the absorbance at 600 nm ($OD_{600}$) and the extent of reaction and product distribution determined by HPLC. The results are presented in Table 1 and Table 2: the sample is identified by the transformant with a suffix notation indicating independent transformants, Gly is glycerol, Glu is D-glucose, Con. is conversion, Sel. is selectivity, Yld is yield, and NA is not applicable. Conversion, selectivity and yield were based on glycerol consumption.

TABLE 1

Production of 1,3-Propanediol from Glycerol

| Sample | $OD_{600}$ | [Gly] (mM) | [1,3-propanediol] (mM) | % Con. | % Sel. | % Yld. |
|---|---|---|---|---|---|---|
| media | NA | 23.0 | 0.0 | NA | NA | NA |
| pKP4-3 | 0.206 | 14.0 | 1.0 | 39 | 11 | 4 |
| pKP4-4 | 0.297 | 12.6 | 1.6 | 45 | 15 | 7 |
| pKP5-1 | 0.242 | 13.4 | 0.8 | 42 | 8 | 4 |
| pKP5-2 | 0.300 | 13.4 | 1.4 | 42 | 15 | 6 |

TABLE 2

Production of 1,3-Propanediol from Glycerol and Glucose

| Sample | $OD_{600}$ | [Gly] (mM) | [Glu] (mM) | [1,3-propanediol] (mM) | % Con. | % Sel. | % Yld. |
|---|---|---|---|---|---|---|---|
| media | NA | 10.7 | 4.3 | 0.0 | NA | NA | NA |
| pKP4-3 | 0.257 | 5.3 | 0.0 | 1.0 | 50 | 19 | 9 |
| pKP4-4 | 0.321 | 3.9 | 0.0 | 1.2 | 64 | 18 | 11 |
| pKP5-1 | 0.366 | 1.5 | 0.2 | 3.6 | 86 | 39 | 34 |
| pKP5-2 | 0.367 | 1.5 | 0.2 | 4.1 | 86 | 45 | 38 |

DNA sequence analysis of pKP4 and pKP5

The size of insert DNA in the case of both pKP4 and pKP5 varied from 25 to 30 Kb. Both clones had certain fragments that were common and certain fragments were different. A 22 kb EcoR1 fragment from pKP4 was eluted from an agarose gel using GeneClean and later digested with BamHI or EcoRV and the various fragments were subcloned into plasmid pIBI31 digested with EcoR1 or BamH1 or HincII. Clones containing inserts were identified and DNA sequence was generated.

The DNA sequence that was generated showed homology to the cob and pocR and pdu genes of S. typhimurium. It is well known that the pdu operon in S. typhimurium codes for genes that are needed for 1,2-propanediol utilization. (Bobik et al., J. Bacteriol, 174, 2253 (1992)). Similarly, it is known that the cob operon encodes genes that are needed for vitamin $B_{12}$ synthesis. Within the pdu operon it is further recognized that the pduC gene encodes for diol dehydratase production.

The region of K. pneumoniae coding for the pdu operon genes is shown in FIG. 1. FIG. 1 is a schematic representation of the gene organization of pdu-cob region of K. pneumoniae. Comparisons were made between this pdu-cob region and the same regions of the gene belonging to S. typhimurium using algorithms provided by Sequence Analysis Software of the University of Wisconsin (Genetics Computer Group, (1991), Version 7, April 1991, 575 Science Drive, Madison, Wis., U.S.A. 53711). A table giving the percent identity and similarity as calculated by the GAP program of the Genetics Computer Group are shown below.

| | Percent Similarity | Percent Identity |
|---|---|---|
| pocR | 90.48% | 84.35% |
| pduA | 100% | 94.85% |
| pduB | 99.16% | 96.64% |
| pduC | 98.31% (partial seq.) | 94.92% |
| pduF | 92.42% | 82.20% |

As can be seen by this comparison, and in FIG. 2, the pduC open reading frame showed extensive homology (98.31%) to the pduC gene of S. typhimurium. pduC was linked to pduF and showed homology to the gene encoding glycerol dehydratase from Citrobacter freundii (FIG. 3).

FIG. 3 is a comparison of the deduced amino acid sequence encoded by the pduC gene from K. pneumoniae (SEQ ID NO.: 5) vs. the amino acid sequence encoded by the glycerol dehydratase gene of C. freundii (SEQ ID NO.: 6). These comparisons showed that the percent similarity was only 84% and the identity only 70%. Thus, the pduC gene encoding for diol dehydratase was a clearly different enzyme and is being used to convert glycerol to 1,3-propanediol in these transformed E. coli strains. The sequence of the gene encoding this diol dehydratase enzyme is given in SEQ ID NO.: 1.

Additionally, another open reading frame has been identified on the pdu gene which showed a high degree of homology with the regions encoding alcohol dehydrogenases. For example, deduced amino acid comparisons showed that this open reading frame had 43% homology with E. coli alcohol dehydrogenase and a 54% homology with the oxidoreductase of C. freundii. This open reading frame had been sequenced and is identified as SEQ ID NO.: 2.

Example 3

Screening E. coli strains, transformed with a cosmid library DNA from K. aerogenes and containing the glycerol dehydratase enzyme that produce 1,3-propanediol Example 3 demonstrated the screening of transformed E. coli cells with cosmid library DNA from K. aerogenes for the presence of an active enzyme that converted glycerol to 1,3-propanediol. Sequencing of the positive clones revealed that each contained a gene with a high degree of homology to the gene encoding 1,2-propanediol dehydratase, endcoded by the pdu operon.

Single colonies of *E. coli* XL1-Blue MR transfected with DNA from *K. aerogenes* were inoculated into microtiter wells containing 200 ul of S15 medium+0.2% glycerol+400 ng per ml of vitamin $B_{12}$+0.001% yeast extract+50 ug/ml ampicillin (50 amp).

Culture supernatant was analyzed for the presence of 1,3-propanediol after 96 h. Two colonies were positive from 2 microtiter plates but after 1 week at room temperature the bacteria were not viable. A third mirotiter plate was inoculated and a master plate containing LB+50 amp was also inoculated. One positive clone labelled KAE3E10 was identified. The masterplate containing KAE3E10 used to replate the positive clone and cosmid DNA was isolated. DH5α cells were transformed with KAE3E10 DNA and transformants were screened for the conversion of glycerol to 1,3-propanediol. KAE3E10 was renamed pKA3 and contained an insert of approximately 40 kb. The DNA sequence of pKA3 showed a region that was homologous to cob and pocR and pdu operon of *S. typhimurium*.

Thus, it appeared that pKA3 also coded for a 1,2-propanediol utilizing operon. Diol dehydratase was presumably responsible for the conversion of glycerol to 1,3-propanediol.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1665 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

```
ATGAGATCGA  AAAGATTTGA  AGCACTGGCG  AAACGCCCTG  TGAATCAGGA  TGGTTTCGTT    60

AAGGAGTGGA  TTGAAGAGGG  CTTTATCGCG  ATGGAAAGTC  CTAACGATCC  CAAACCTTCT   120

ATCCGCATCG  TCAACGGCGC  GGTGACCGAA  CTCGACGGTA  AACCGGTTGA  GCAGTTCGAC   180

CTGATTGACC  ACTTTATCGC  GCGCTACGGC  ATTAATCTCG  CCCGGGCCGA  AGAAGTGATG   240

GCCATGGATT  CGGTTAAGCT  CGCCAACATG  CTCTGCGACC  CGAACGTTAA  ACGCAGCGAC   300

ATCGTGCCGC  TCACTACCGC  GATGACCCCG  GCGAAAATCG  TGGAAGTGGT  GTCGCATATG   360

AACGTGGTCG  AGATGATGAT  GGCGATGCAA  AAAATGCGCG  CCCGCCGCAC  GCCGTCCCAG   420

CAGGCGCATG  TCACTAATAT  CAAAGATAAT  CCGGTACAGA  TTGCCGCCGA  CGCCGCTGAA   480

GGCGCATGGC  GCGGCTTTGA  CGAACAGGAG  ACCACCGTCG  CCGTGGCGCG  CTACGCGCCG   540

TTCAACGCCA  TCGCCCTGCT  GGTGGGTTCA  CAGGTTGGCC  GCCCCGGCGT  CCTCACCCAG   600

TGTTCGCTGG  AAGAAGCCAC  CGAGCTGAAA  CTGGGCATGC  TGGGCCACAC  CTGCTATGCC   660

GAAACCATTT  CGGTATACGG  TACGGAACCG  GTGTTTACCG  ATGGCGATGA  CACTCCATGG   720

TCGAAAGGCT  TCCTCGCCTC  CTCCTACGCC  TCGCGCGGCC  TGAAAATGCG  CTTTACCTCC   780

GGTTCCGGTT  CTGAAGTACA  GATGGGCTAT  GCCGAAGGCA  AATCGATGCT  TTATCTCGAA   840

GCGCGCTGCA  TCTACATCAC  CAAAGCCGCC  GGGGTGCAAG  GCCTGCAGAA  TGGCTCCGTC   900

AGCTGTATCG  GCGTACCGTC  CGCCGTGCCG  TCCGGATCC   GCGCCGTACT  GGCGGAAAAC   960

CTGATCTGCT  CAGCGCTGGA  TCTGGAGTGC  GCCTCCAGCA  ACGATCAAAC  CTTTACCCAC  1020

TCGGATATGC  GGCGTACCGC  GCGTCTGCTG  ATGCAGTTCC  TGCCAGGCAC  CGACTTCATC  1080

TCCTCCGGTT  ACTCGGCGGT  GCCCAACTAC  GACAACATGT  TCGCCGGTTC  CAACGAAGAT  1140

GCCGAAGACT  TCGATGACTA  CAACGTGATC  CAGCGCGACC  TGAAGGTCGA  TGGCGGCCTG  1200
```

```
CGGCCGGTGC  GTGAAGAGGA  CGTGATCGCC  ATTCGCAACA  AAGCCGCCCG  CGCGCTGCAG      1260

GCGGTATTTG  CCGGCATGGG  TTTGCCGCCT  ATTACGGATG  AAGAGGTAGA  AGCCGCCACC      1320

TACGCCCACG  GTTCAAAAGA  TATGCCTGAG  CGCAATATCG  TCGAGGACAT  CAAGTTTGCT      1380

CAGGAGATCA  TCAACAAGAA  CCGCAACGGC  CTGGAGGTGG  TGAAAGCCCT  GGCGAAAGGC      1440

GGCTTCCCCG  ATGTCGCCCA  GGACATGCTC  AATATTCAGA  AAGCCAAGCT  CACCGGCGAC      1500

TACCTGCATA  CCTCCGCCAT  CATTGTTGGC  GAGGGCCAGG  TGCTCTCGGC  CGTGAATGAC      1560

GTGAACGATT  ATGCCGGTCC  GGCAACAGGC  TACCGCCTGC  AAGGCGAGCG  CTGGGAAGAG      1620

ATTAAAAATA  TCCCGGGCGC  GCTCGATCCC  AATGAACTTG  GCTAA                      1665
```

(2) INFORMATION FOR SEQ ID NO:2:

(i) SEQUENCE CHARACTERISTICS:
        (A) LENGTH: 1335 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

```
ATGCATACCT  TTTCTCTGCA  AACGCGCCTC  TACAGCGGCC  CGGGCAGCCT  GGCCGCGCTG        60

CAGCGCTTTA  GCCATCAGCA  CATCTGGATC  GTCTGCGACG  GCTTCCTGGC  GCGCTCGCCG       120

CTGCTTGACC  GACTGCGCGC  CGCGCTGCCC  GCCAGCAACC  GCGTCAGCGT  GTTCAGCGAT       180

ATTACACCGG  ATCCGACCAT  TCACACCGTG  GCGAAAGGGA  TAGCGCAGAT  GCAGGCCCTG       240

CGTCCGCAGG  TGGTGATCGG  CTTCGGCGGC  GGCTCGGCGA  TGGATGCCGC  CAAGGCTATC       300

GTCTGGTTCA  GCCAGCAGGG  CGGTCTGCCT  GTTGACACCT  GCGTGGCGAT  CCCCACCACC       360

AGCGGTACCG  GTTCGGAAGT  GACCAGCGCC  TGCGTCATCA  GCGACCCGGA  AAAAGGGATC       420

AAGTACCCGC  TGTTCCATGA  GGCGCTCTGT  CCCGACATGG  CGATCATCGA  CCCGACGCTG       480

GTGGTTAGCG  TACCGCCCAC  CATCACAGCC  CATACCGGGC  TGGACGCGCT  GACCCACGCC       540

CTGGAGGCAT  GGGTCTCGCC  GCAGGCCACC  GATTTTACCG  ATGCGCTGGC  GGAAAAGGCC       600

GCCAGGCTGG  TGTTTCGCGC  CCTGCCCGTT  GCGATTCGTC  AGGGCGACTG  CATTGCGACC       660

CGCAGCAAAA  TGCACAATGC  ATCAACCCTC  GCCGGTATGG  CCTTTAGCCA  GGCTGGCCTT       720

GGGCTCAATC  ATGCGATCGC  CCATCAGCTT  GGCGGCCAGT  TTCACCTCCC  CCATGGCCTG       780

GCCAATGCGC  TGCTGCTGAC  CGCGGTGATC  CGCTTCAATG  CCGGCGAGCC  GCGAGCGGCT       840

AAGCGCTATG  CACGCCTGGC  CAGGGCCTAC  CGCTTCTGCC  CGCCCGCAGC  TGGCGAACAG       900

GAGGCTTTCC  AGGCGCTGCT  TACCGCGGTG  AAACGCTGA   ACAGCAGTG   CGCCATTCCC       960

CCCCTCAAGG  GCGCGCTGCA  GGAAAAGTAT  CCCCTTTTCT  TATCGCATCA  ACCAGTTCAA      1020

CATCATTGCT  CAGACGCACC  TGCCCGCACA  GCACGAAACC  GACCAGGTGG  CCGGCAATCA      1080

CCAGCGGGAT  GGAAAAATCG  GTTAACCCCG  CATGACAGCG  GTAGATACAC  AGCTGTCTTT      1140

TTTCGAGGCT  TCCAGCCCGC  CGCAGCGGTC  GCTCATGCGA  CAGCGTCCGC  TGTGCTCCGG      1200

GTGCTGACGC  ATCAGCTGGC  AAAACGGCGT  GAAATTAAAC  AATTCAGAAA  TCTCATCACC      1260

GTGAATATTG  ACGACCACAA  CCGCCAGACT  GGTGGCTTGC  GCAAAATCCT  GTGCGATTTT      1320

ATTGATGAGT  TCTGA                                                           1335
```

(2) INFORMATION FOR SEQ ID NO:3:

( i ) SEQUENCE CHARACTERISTICS:
   ( A ) LENGTH: 100 amino acids
   ( B ) TYPE: amino acid
   ( C ) STRANDEDNESS: unknown
   ( D ) TOPOLOGY: unknown ( i i ) MOLECULE TYPE: peptide ( i i i ) HYPOTHETICAL: NO ( x i ) SEQUENCE DESCRIPTION: SEQ ID NO:3:

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Arg Ile Val Asn Gly Ala Val
        35                  40                  45

Thr Glu Leu Asp Gly Lys Pro Val Glu Gln Phe Asp Leu Ile Asp His
    50                  55                  60

Phe Ile Ala Arg Tyr Gly Ile Asn Leu Ala Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Asp
            100
```

( 2 ) INFORMATION FOR SEQ ID NO:4:

( i ) SEQUENCE CHARACTERISTICS:
      ( A ) LENGTH: 59 amino acids
      ( B ) TYPE: amino acid
      ( C ) STRANDEDNESS: unknown
      ( D ) TOPOLOGY: unknown ( i i ) MOLECULE TYPE: peptide ( i i i ) HYPOTHETICAL: NO ( x i ) SEQUENCE DESCRIPTION: SEQ ID NO:4:

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe
    50                  55
```

( 2 ) INFORMATION FOR SEQ ID NO:5:

( i ) SEQUENCE CHARACTERISTICS:
      ( A ) LENGTH: 554 amino acids
      ( B ) TYPE: amino acid
      ( C ) STRANDEDNESS: unknown
      ( D ) TOPOLOGY: unknown ( i i ) MOLECULE TYPE: peptide ( i i i ) HYPOTHETICAL: NO ( x i ) SEQUENCE DESCRIPTION: SEQ ID NO:5:

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
```

```
                    20                          25                          30
Ser  Pro  Asn  Asp  Pro  Lys  Pro  Ser  Ile  Arg  Ile  Val  Asn  Gly  Ala  Val
               35                       40                    45

Thr  Glu  Leu  Asp  Gly  Lys  Pro  Val  Glu  Gln  Phe  Asp  Leu  Ile  Asp  His
     50                       55                       60

Phe  Ile  Ala  Arg  Tyr  Gly  Ile  Asn  Leu  Ala  Arg  Ala  Glu  Glu  Val  Met
65                       70                  75                              80

Ala  Met  Asp  Ser  Val  Lys  Leu  Ala  Asn  Met  Leu  Cys  Asp  Pro  Asn  Val
               85                       90                    95

Lys  Arg  Ser  Asp  Ile  Val  Pro  Leu  Thr  Thr  Ala  Met  Thr  Pro  Ala  Lys
              100                      105                  110

Ile  Val  Glu  Val  Val  Ser  His  Met  Asn  Val  Val  Glu  Met  Met  Met  Ala
          115                      120                  125

Met  Gln  Lys  Met  Arg  Ala  Arg  Arg  Thr  Pro  Ser  Gln  Gln  Ala  His  Val
     130                      135                      140

Thr  Asn  Ile  Lys  Asp  Asn  Pro  Val  Gln  Ile  Ala  Ala  Asp  Ala  Ala  Glu
145                      150                      155                      160

Gly  Ala  Trp  Arg  Gly  Phe  Asp  Glu  Gln  Glu  Thr  Thr  Val  Ala  Val  Ala
               165                      170                      175

Arg  Tyr  Ala  Pro  Phe  Asn  Ala  Ile  Ala  Leu  Leu  Val  Gly  Ser  Gln  Val
               180                      185                 190

Gly  Arg  Pro  Gly  Val  Leu  Thr  Gln  Cys  Ser  Leu  Glu  Glu  Ala  Thr  Glu
          195                      200                      205

Leu  Lys  Leu  Gly  Met  Leu  Gly  His  Thr  Cys  Tyr  Ala  Glu  Thr  Ile  Ser
     210                      215                      220

Val  Tyr  Gly  Thr  Glu  Pro  Val  Phe  Thr  Asp  Gly  Asp  Asp  Thr  Pro  Trp
225                      230                      235                      240

Ser  Lys  Gly  Phe  Leu  Ala  Ser  Ser  Tyr  Ala  Ser  Arg  Gly  Leu  Lys  Met
               245                      250                      255

Arg  Phe  Thr  Ser  Gly  Ser  Gly  Ser  Glu  Val  Gln  Met  Gly  Tyr  Ala  Glu
               260                      265                      270

Gly  Lys  Ser  Met  Leu  Tyr  Leu  Glu  Ala  Arg  Cys  Ile  Tyr  Ile  Thr  Lys
          275                      280                      285

Ala  Ala  Gly  Val  Gln  Gly  Leu  Gln  Asn  Gly  Ser  Val  Ser  Cys  Ile  Gly
     290                      295                      300

Val  Pro  Ser  Ala  Val  Pro  Ser  Gly  Ile  Arg  Ala  Val  Leu  Ala  Glu  Asn
305                      310                      315                      320

Leu  Ile  Cys  Ser  Ala  Leu  Asp  Leu  Glu  Cys  Ala  Ser  Ser  Asn  Asp  Gln
               325                      330                      335

Thr  Phe  Thr  His  Ser  Asp  Met  Arg  Arg  Thr  Ala  Arg  Leu  Leu  Met  Gln
               340                      345                      350

Phe  Leu  Pro  Gly  Thr  Asp  Phe  Ile  Ser  Ser  Gly  Tyr  Ser  Ala  Val  Pro
          355                      360                      365

Asn  Tyr  Asp  Asn  Met  Phe  Ala  Gly  Ser  Asn  Glu  Asp  Ala  Glu  Asp  Phe
     370                      375                      380

Asp  Asp  Tyr  Asn  Val  Ile  Gln  Arg  Asp  Leu  Lys  Val  Asp  Gly  Gly  Leu
385                      390                      395                      400

Arg  Pro  Val  Arg  Glu  Glu  Asp  Val  Ile  Ala  Ile  Arg  Asn  Lys  Ala  Ala
               405                      410                      415

Arg  Ala  Leu  Gln  Ala  Val  Phe  Ala  Gly  Met  Gly  Leu  Pro  Pro  Ile  Thr
          420                      425                      430

Asp  Glu  Glu  Val  Glu  Ala  Ala  Thr  Tyr  Ala  His  Gly  Ser  Lys  Asp  Met
     435                      440                      445
```

```
Pro  Glu  Arg  Asn  Ile  Val  Glu  Asp  Ile  Lys  Phe  Ala  Gln  Glu  Ile  Ile
     450                 455                      460

Asn  Lys  Asn  Arg  Asn  Gly  Leu  Glu  Val  Val  Lys  Ala  Leu  Ala  Lys  Gly
465                      470                      475                      480

Gly  Phe  Pro  Asp  Val  Ala  Gln  Asp  Met  Leu  Asn  Ile  Gln  Lys  Ala  Lys
                    485                 490                      495

Leu  Thr  Gly  Asp  Tyr  Leu  His  Thr  Ser  Ala  Ile  Ile  Val  Gly  Glu  Gly
               500                 505                           510

Gln  Val  Leu  Ser  Ala  Val  Asn  Asp  Val  Asn  Asp  Tyr  Ala  Gly  Pro  Ala
          515                 520                      525

Thr  Gly  Tyr  Arg  Leu  Gln  Gly  Glu  Arg  Trp  Glu  Glu  Ile  Lys  Asn  Ile
     530                 535                      540

Pro  Gly  Ala  Leu  Asp  Pro  Asn  Glu  Leu  Gly
545                      550
```

( 2 ) INFORMATION FOR SEQ ID NO:6:

( i ) SEQUENCE CHARACTERISTICS:
        ( A ) LENGTH: 555 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:6:

```
Met  Arg  Arg  Ser  Lys  Arg  Phe  Glu  Val  Leu  Ala  Gln  Arg  Pro  Val  Asn
1                   5                   10                      15

Gln  Asp  Gly  Leu  Ile  Gly  Glu  Trp  Pro  Glu  Glu  Gly  Leu  Ile  Ala  Met
               20                  25                           30

Glu  Ser  Pro  Tyr  Asp  Pro  Ala  Ser  Ser  Val  Lys  Val  Glu  Asn  Gly  Arg
          35                  40                       45

Ile  Val  Glu  Leu  Asp  Gly  Lys  Ser  Arg  Ala  Glu  Phe  Asp  Met  Ile  Asp
     50                  55                       60

Arg  Phe  Ile  Ala  Asp  Tyr  Ala  Ile  Asn  Val  Pro  Glu  Ala  Glu  Arg  Ala
65                       70                       75                       80

Met  Gln  Leu  Asp  Ala  Leu  Glu  Ile  Ala  Arg  Met  Leu  Val  Asp  Ile  His
               85                       90                           95

Val  Ser  Arg  Glu  Glu  Ile  Ile  Ala  Ile  Thr  Thr  Ala  Ile  Thr  Pro  Ala
               100                      105                          110

Lys  Arg  Leu  Glu  Val  Met  Ala  Gln  Met  Asn  Val  Val  Glu  Met  Met  Met
          115                 120                      125

Ala  Leu  Gln  Lys  Met  Arg  Ala  Arg  Arg  Thr  Pro  Ser  Asn  Gln  Cys  His
     130                 135                      140

Val  Thr  Asn  Leu  Lys  Asp  Asn  Pro  Val  Gln  Ile  Ala  Ala  Asp  Ala  Ala
145                      150                      155                      160

Glu  Ala  Gly  Ile  Arg  Gly  Phe  Ser  Glu  Gln  Glu  Thr  Thr  Val  Gly  Ile
                    165                 170                      175

Ala  Arg  Tyr  Ala  Pro  Phe  Asn  Ala  Leu  Ala  Leu  Leu  Val  Gly  Ser  Gln
               180                      185                      190

Cys  Gly  Ala  Pro  Gly  Val  Leu  Thr  Gln  Cys  Ser  Val  Glu  Glu  Ala  Thr
          195                 200                      205

Glu  Leu  Glu  Leu  Gly  Met  Arg  Gly  Leu  Thr  Ser  Tyr  Ala  Glu  Thr  Val
     210                 215                      220

Ser  Val  Tyr  Gly  Thr  Glu  Ser  Val  Phe  Thr  Asp  Gly  Asp  Asp  Thr  Pro
225                      230                      235                      240
```

```
Trp Ser Lys Ala Phe Leu Ala Ser Ala Tyr Ala Ser Arg Gly Leu Lys
            245                 250                 255
Met Arg Tyr Thr Ser Gly Thr Gly Ser Glu Ala Leu Met Gly Tyr Ser
            260                 265                 270
Glu Ser Lys Ser Met Leu Tyr Leu Glu Ser Arg Cys Ile Phe Ile Thr
        275                 280                 285
Lys Gly Ala Gly Val Gln Gly Leu Gln Asn Gly Ala Val Ser Cys Ile
    290                 295                 300
Gly Met Thr Gly Ala Val Pro Ser Gly Ile Arg Ala Val Leu Ala Glu
305                 310                 315                 320
Asn Leu Ile Ala Ser Met Leu Asp Leu Glu Val Ala Ser Ala Asn Asp
                325                 330                 335
Gln Thr Phe Ser His Ser Asp Ile Arg Arg Thr Ala Arg Thr Leu Met
            340                 345                 350
Gln Met Leu Pro Gly Thr Asp Phe Ile Phe Ser Gly Tyr Ser Ala Val
            355                 360                 365
Pro Asn Tyr Asp Asn Met Phe Ala Gly Ser Asn Phe Asp Ala Glu Asp
    370                 375                 380
Phe Asp Asp Tyr Asn Ile Leu Gln Arg Asp Leu Met Val Asp Gly Gly
385                 390                 395                 400
Leu Arg Pro Val Thr Glu Glu Glu Thr Ile Ala Ile Arg Asn Lys Ala
                405                 410                 415
Ala Arg Ala Ile Gln Ala Val Phe Arg Glu Leu Gly Leu Pro Leu Ile
            420                 425                 430
Ser Asp Glu Glu Val Asp Ala Ala Thr Tyr Ala His Gly Ser Lys Asp
            435                 440                 445
Met Pro Ala Arg Asn Val Val Glu Asp Leu Ala Ala Val Glu Glu Met
    450                 455                 460
Met Lys Arg Asn Ile Thr Gly Leu Asp Ile Val Gly Ala Leu Ser Ser
465                 470                 475                 480
Ser Gly Phe Glu Asp Ile Ala Ser Asn Ile Leu Asn Met Leu Arg Gln
                485                 490                 495
Arg Val Thr Gly Asp Tyr Leu Gln Thr Ser Ala Ile Leu Asp Arg Gln
            500                 505                 510
Phe Asp Val Val Ser Ala Val Asn Asp Ile Asn Asp Tyr Gln Gly Pro
        515                 520                 525
Gly Thr Gly Tyr Arg Ile Ser Ala Glu Arg Trp Ala Glu Ile Lys Asn
    530                 535                 540
Ile Ala Gly Val Val Gln Pro Gly Ser Ile Glu
545                 550                 555
```

( 2 ) INFORMATION FOR SEQ ID NO:7:

( i ) SEQUENCE CHARACTERISTICS:
        ( A ) LENGTH: 131 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:7:

```
Arg Ala Val Leu Ala Glu Asn Leu Ile Ala Ser Met Leu Asp Leu Glu
1               5                   10                  15
Val Ala Ser Ala Asn Asp Gln Thr Phe Ser His Ser Asp Ile Arg Arg
```

|   |   |   |   | 20 |   |   |   | 25 |   |   |   | 30 |   |   |
|---|---|---|---|---|---|---|---|---|---|---|---|---|---|---|
| Thr | Ala | Arg<br>35 | Thr | Leu | Met | Gln | Met<br>40 | Leu | Pro | Gly | Thr | Asp<br>45 | Phe | Ile | Phe |
| Ser | Gly<br>50 | Tyr | Ser | Ala | Val | Pro<br>55 | Asn | Tyr | Asp | Asn | Met<br>60 | Phe | Ala | Gly | Ser |
| Asn<br>65 | Phe | Asp | Ala | Glu | Asp<br>70 | Phe | Asp | Asp | Tyr | Asn<br>75 | Ile | Leu | Gln | Arg | Asp<br>80 |
| Leu | Met | Val | Asp | Gly<br>85 | Gly | Leu | Arg | Pro | Val<br>90 | Thr | Glu | Ala | Glu | Thr<br>95 | Ile |
| Ala | Ile | Arg | Gln<br>100 | Lys | Ala | Ala | Arg | Ala<br>105 | Ile | Gln | Ala | Val | Phe<br>110 | Arg | Glu |
| Leu | Gly | Leu<br>115 | Pro | Pro | Ile | Ala | Asp<br>120 | Glu | Glu | Val | Glu | Ala<br>125 | Ala | Thr | Tyr |
| Ala | Gln | Gly<br>130 |   |   |   |   |   |   |   |   |   |   |   |   |   |

(2) INFORMATION FOR SEQ ID NO:8:

(i) SEQUENCE CHARACTERISTICS:
        (A) LENGTH: 150 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:8:

| Val<br>1 | Ser | Cys | Ile | Gly<br>5 | Met | Thr | Gly | Ala | Val<br>10 | Pro | Ser | Gly | Ile | Arg<br>15 | Ala |
|---|---|---|---|---|---|---|---|---|---|---|---|---|---|---|---|
| Val | Leu | Ala | Glu<br>20 | Asn | Leu | Ile | Ala | Ser<br>25 | Met | Leu | Asp | Leu | Glu<br>30 | Val | Ala |
| Ser | Ala | Asn<br>35 | Asp | Gln | Thr | Phe | Ser<br>40 | His | Ser | Asp | Ile | Arg<br>45 | Arg | Thr | Ala |
| Arg | Thr<br>50 | Leu | Met | Gln | Met | Leu<br>55 | Pro | Gly | Thr | Asp | Phe<br>60 | Ile | Phe | Ser | Gly |
| Tyr<br>65 | Ser | Ala | Val | Pro | Asn<br>70 | Tyr | Asp | Asn | Met | Phe<br>75 | Ala | Gly | Ser | Asn | Phe<br>80 |
| Asp | Ala | Glu | Asp | Phe<br>85 | Asp | Asp | Tyr | Asn | Ile<br>90 | Leu | Gln | Arg | Asp | Leu<br>95 | Met |
| Val | Asp | Gly | Gly<br>100 | Leu | Arg | Pro | Val | Thr<br>105 | Glu | Glu | Glu | Thr | Ile<br>110 | Ala | Ile |
| Arg | Asn | Lys<br>115 | Ala | Ala | Arg | Ala | Ile<br>120 | Gln | Ala | Val | Phe | Arg<br>125 | Glu | Leu | Gly |
| Leu | Pro<br>130 | Leu | Ile | Ser | Asp | Glu<br>135 | Glu | Val | Asp | Ala | Ala<br>140 | Thr | Tyr | Ala | His |
| Gly<br>145 | Ser | Lys | Asp | Met | Pro<br>150 |   |   |   |   |   |   |   |   |   |   |

Figure 5:
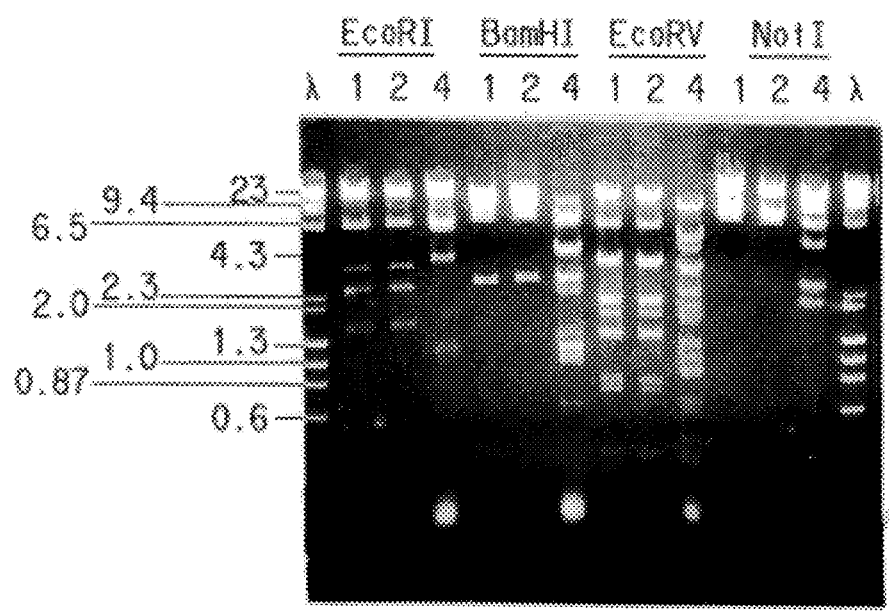
FIG. 5 depicts restriction digests (EcoR 1, BamH 1, EcoR V and Not1) of cosmids pKP1, pKP2 and pKP4, labeled as columns 1, 2 and 4 respectively, and separation on a 0.8% agarose gel electrophoresis. Molecular size markers were loaded on the lanes in the end. Columns labeled as number 4 represent the cosmid containing a diol dehydratase enzyme.

What is claimed is:

1. A cosmid comprising a DNA fragment of about 35 kb isolated from *Klebsiella pneumoniae* wherein said fragment encodes an active diol dehydratase enzyme having the restriction digest in FIG. 5, columns numbered 4, said cosmid contained within a transformed *E. coli* deposited with the American Type Culture Collection under accession number ATCC 69790.

2. A transformed microorganism comprising a host microorganism and the cosmid of claim 1.

3. The transformed microorganism of claim 2 wherein the host microorganism is *E. coli*, and which is deposited with the American Type Culture Collection as accession number ATCC 69790.

4. The cosmid of claim 1 which when transformed into bacteria causes metabolism of glycerol to 1,3-propanediol.

5. A transformed microorganism comprising a host microorganism and a DNA fragment of the cosmid of claim 1, said fragment encoding an active functional protein.

6. A DNA fragment comprising a gene encoding a diol dehydratase enzyme, said gene encompassed by the cosmid of claim 1.

7. A isolated gene encoding an active diol dehydratase enzyme comprising a contiguous sequence which consists of SEQ ID NO: 1.

8. A isolated gene encoding an active alcohol dehydrogenase comprising a contiguous sequence which consists of SEQ ID NO: 2.

9. A transformed microorganism comprising a host microorganism and the heterologous gene of claim 7 or claim 8.

10. A transformed microorganism comprising $E.\ coli$ DH5α and the DNA sequence of claim 7 or claim 8.

* * * * *

UNITED STATES PATENT AND TRADEMARK OFFICE
CERTIFICATE OF CORRECTION

PATENT NO. : 5,633, 362
DATED : May 27, 1997
INVENTOR(S) : Vasantha Nagarajan et al.

It is certified that error appears in the above-identified patent and that said Letters Patent is hereby corrected as shown below:

In the drawings, Figure 1, the text reading "pocE" should be deleted and replaced with --pocR--.

Signed and Sealed this

Twenty-fifth Day of November, 1997

Attest:

BRUCE LEHMAN

Attesting Officer

Commissioner of Patents and Trademarks